Figure 1:
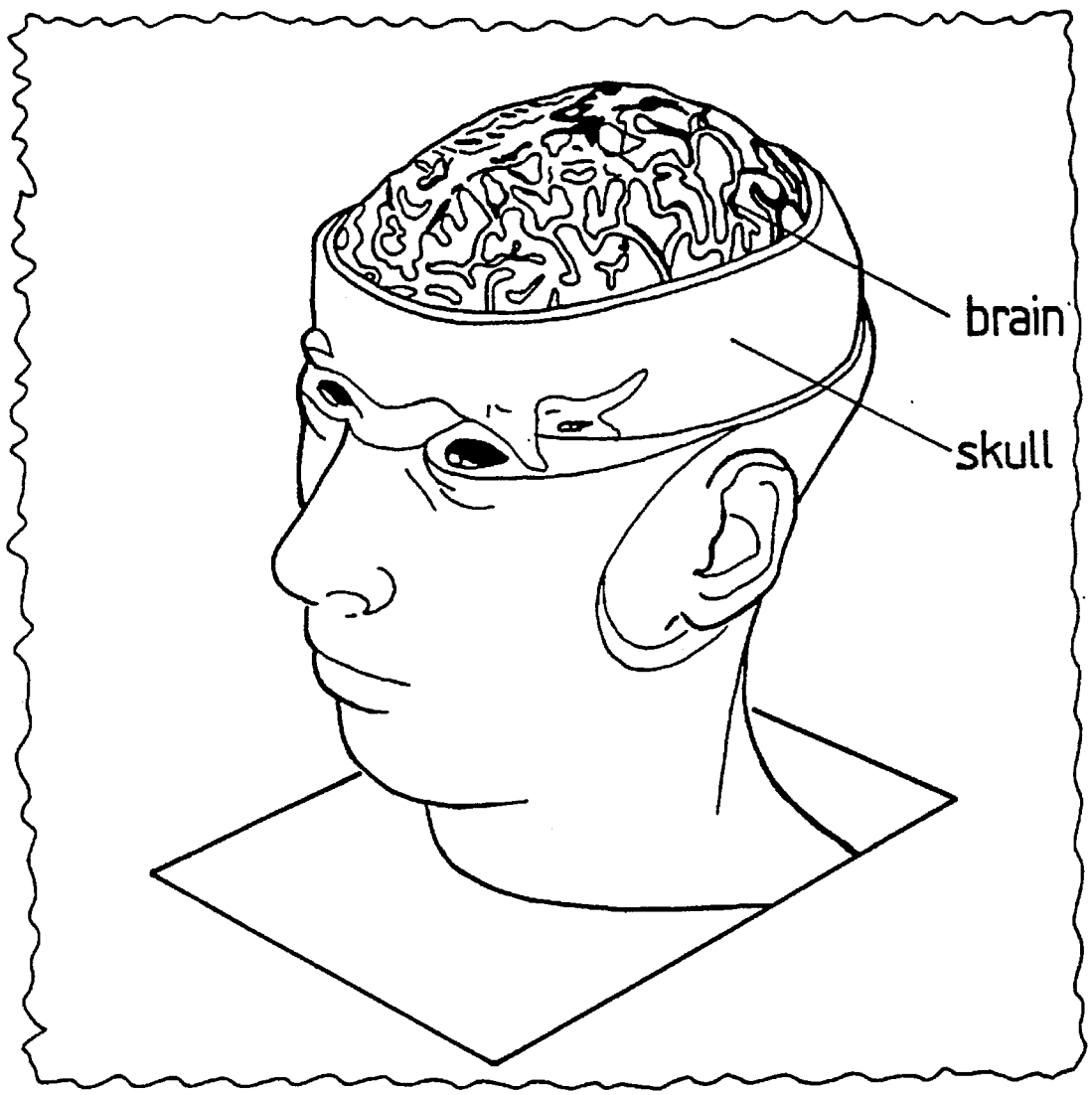

US005623586A

United States Patent [19]
Höhne

[11] Patent Number: 5,623,586
[45] Date of Patent: Apr. 22, 1997

[54] METHOD AND DEVICE FOR KNOWLEDGE BASED REPRESENTATION AND DISPLAY OF THREE DIMENSIONAL OBJECTS

[76] Inventor: Karl-Heinz Höhne, Friedrich-Ebert-Strasse 10 e, 2080 Pinneberg, Germany

[21] Appl. No.: 163,585

[22] Filed: Dec. 6, 1993

Related U.S. Application Data

[63] Continuation of Ser. No. 887,706, May 22, 1992, abandoned.

[30] Foreign Application Priority Data

May 25, 1991 [DE] Germany .......................... 41 17 117.9

[51] Int. Cl.⁶ ..................................................... G06T 7/60
[52] U.S. Cl. ........................................... 395/124; 395/326
[58] Field of Search .................................... 395/121, 124, 395/120, 161; 340/723; 364/413.13, 413.19, 413.22; 382/131, 132

[56] References Cited

U.S. PATENT DOCUMENTS

| | | | |
|---|---|---|---|
| 4,879,668 | 11/1989 | Cline et al. | 395/124 |
| 4,888,583 | 12/1989 | Ligocki et al. | 340/729 |
| 4,914,589 | 4/1990 | Crawford | 364/43.17 |
| 4,945,478 | 7/1990 | Mericke et al. | 364/413.22 |
| 4,985,834 | 1/1991 | Cline et al. | 364/413.22 |
| 5,185,809 | 2/1993 | Kennedy et al. | 382/131 |
| 5,293,313 | 3/1994 | Cecil et al. | 382/131 X |

FOREIGN PATENT DOCUMENTS

| | | |
|---|---|---|
| 0216156 | 4/1987 | European Pat. Off. . |
| 2853560 | 6/1979 | Germany . |
| 2804732 | 1/1985 | Germany . |
| 3414566 | 7/1987 | Germany . |

OTHER PUBLICATIONS

Microsoft Excel User's Guide, 1990, p. 396.
Ch. Sohn, et al, "Dreidimensionale Darstellung in der Ultraschalldiagnostik" in *Deutsche Medizinische Wochenschrift*, Nr. 45, 113 Jahrgang, Nov. 11, 1988, pp. 1743–1747.
R. A. Robb et al, "Interactive Display and Analysis of 3-D Medical Images" in *IEEE Transactions On Medical Imaging*, vol. 8, No. 3, Sep. 1989, pp. 217–226.
Richard A. Robb, "Three–Dimensional Biomedical Imaging", CRC Press, Inc. Boca Raton, Florida, vol. II, 1985, pp. 125–144.

*Primary Examiner*—Mark K. Zimmerman
*Attorney, Agent, or Firm*—Harness, Dickey & Pierce, P.L.C.

[57] ABSTRACT

The method serves to represent a three dimensional object and is especially adapted for use in the field of medical technology. At least a portion of the object is spatially recorded relative to at least one geometric parameter. Hereby a sequence of picture units is generated. The spatial assignment of the parameter is stored in a storage device and conveyed for visualization to a display device. After acquisition of at least one portion of the space assigned to the object the object is subdivided into volume elements, the coordinates of the volume elements as well as at least one attribute characterizing the volume elements is subsequently stored. Subsequently an assignment of the volume elements to spatial substructures with help of the attributes is performed and at visualization a selectable assignment of the volume elements is realized in dependence of at least one of the attributes.

24 Claims, 10 Drawing Sheets

METHOD AND DEVICE FOR KNOWLEDGE BASED REPRESENTATION AND DISPLAY OF THREE DIMENSIONAL OBJECTS

This is a continuation of U.S. patent application Ser. No. 07/887,706, filed May 22, 1992, now abandoned.

The invention relates to a method for representation of a three dimensional object, especially for use in the field of medical technology, in which at least a portion of the object is acquired spatially relative to at least one geometric parameter, a sequence of picture units generated, the spatial coordination of these parameters stored in a storage device and supplied to the equipment for visualization.

The invention further relates to a device for the representation of three dimensional objects, especially for use in the field of medical technology, which has at least one storage device containing measured value volume information and is connected to a representation device.

With such a method it is possible to record a sequence of sectional pictures of an object and to file them in an image storage device. Especially with a computer supported analysis of these picture sequences is it possible to define cuts through the object which is determined by picture sequences according to freely chosen selectable coordinates and by way of a suitable combining method to determine a new sectional picture. The interpretation of such a sectional picture is, however, subject to considerable problems because the picture sequence yields comparatively arbitrarily generated sectional pictures, picture information which even to a specialist includes few familiar structures and therefore can only be assigned with great difficulty.

With the classical method of representation of three dimensional objects, external views of an object or sectional pictures are represented and for use with an atlas they are provided with descriptions and comments. The respective textual assignments are then fixedly coupled with the sectional pictures and external views, rendering any adjustment time consuming.

It has, however, already been proposed to provide atlases of the sort wherein the respective figures or photographs are digitally stored. The abovementioned sectional pictures can be stored in these atlases and combined with projectable graphic elements. Furthermore it has been proposed to interpret in addition to pure cross-sectional image sequences, information with respect to surface contours and thereby facilitate the interpretation in the case of an arbitrary sectional picture orientation or again also to generate surface representations.

With help of the known methods it is not adequately possible, when arbitrarily selectable sections of the object may be selected, to automatically generate an arbitrary representation such that the meaning of the object is consistently automatically associated.

Therefore it is an object of invention to improve the method of the aforementioned sort in that due to the stored meaning of the detailed substructures arbitrarily differing views can automatically be provided and the information regarding the structures in every section of the view remains constantly associable.

This objective will be achieved by the invention that after the recording of at least one area of a space associated to an object is broken down into volume elements, the coordinates of the volume elements and at least one of the attributes characterizing the volume element is stored and subsequently an assignment of the volume elements to spatial sub-structures is performed as well as for visualization of a selectable assignment of the volume elements as a function of at least one of the attributes is realized.

A further object of the present invention is to provide a device of the aforementioned sort adapted to execute the method of the present invention.

This object will be met in that a separator is provided which subdivides the measured value volume information into volume elements, which separator distributes measured value volume information in a measured value volume storage and is connected to a control unit, which then is linked to the attribute storage, which stores the attributes corresponding to the volume elements, which will be combined with the coordinates of the volume elements in the area of the control unit and that the representation unit is connected with the control unit over a transference span.

By subdividing an object into volume elements and coordinating the attributes to these volume elements, it is possible to deal with any fine subdivision of an object into informational units and subsequently to combine these informational units for a visualization. The informational content is thus not limited to surface contours, but instead includes the complete three dimensional structure of the object. So it is possible within arbitrarily produced sections to automatically mark volume elements assigned to certain structures and, for example, represent them by variously colored markings so as to make them more easily distinguishable.

According to a preferred embodiment of the invention, it is proposed to store the meaning of the respective attributes as textual information which can be combined with the volume elements for visualization. Such a combination of graphic elements and textual information easily enables generating medical or biological atlases with help of the method and device. When the structure of the volume elements has been incorporated once, arbitrary representations can consequently be generated. It is also possible to provide a learning system with a computer supported interpretation which could, for example, enable a university student to gain detailed information about body parts or organs. By subdivision into volume elements it is, for example, possible in regard to a selectable sectional surface to eliminate all volume elements which lie in front of the sectional surface and which are not characterized by one or more attributes that could correspond for example to a specific represented element of the body as described for example in FIGS. 1, 2, 6 and 9. With these means, procedural methods of operations and stereotactic procedures may be practiced. For radiologists, such representations may also be used as references for actual cases.

Because the representation includes projections such as x-ray projections, artificial x-ray pictures can also be produced from the volumes, whereby, because the attribute on each place of the projection picture is subsequently identifiable as to which anatomical structure respectively contributes to intensity value. The interpretation of x-ray pictures can also be facilitated with such representations. An effective execution of the method can be of especial significance if, for example, as in preparation for an operation or therapy, a body part of a patient should be incorporated, a subsequent visualization can afford the doctor who is later to perform the operation the possibilities of the disposition before beginning an operation, enabling him to acquire very extensive information about the object being presented to him for operation. It is especially possible to simulate essential portions of a planned operation with a computer supported visualization and thereby recognize potential problems before endangering a patient and to possibly avoid these potential dangers during the actual operation.

According to another preferred embodiment of the invention, it is suggested that the volume elements be determined from two dimensional sectional pictures after an interpolation between measured value volume information. The sectional pictures are comparatively easy to produce with help of known techniques such as tomography, x-ray techniques or microscope techniques, and with an adequately tight sequence of sectional pictures, yield no relevant loss of information through interpolation. Aside from an sectional picture type incorporation of an object provided with gap space, it is also possible to produce a sectional picture process of a given thickness and to directly contiguously join this to a sectional picture sequence. With such a recording with a measurement device, interpolation becomes unnecessary. Finally, it is also possible, instead of recording an object with a measurement device, to provide a manual application of contour and volume information and to process this manually presented information with help of a control unit.

According to another preferred embodiment of the invention, a structured attribute combination is provided. This makes it possible to structure the visualized information about the object with a respectively suitable resolution. First of all, it is possible to represent a complete system of vessels taken from the surrounding tissue, and with further subsequent refinement, it can be reduced down so as to deal with a special selected single element. It is especially suitable here to consider anatomically defined morphological or structures defining functions when assigning the attributes. It is also possible to provide a hierarchically structured attribute combination. Furthermore, other structurings are also possible, eg. network type coordinations.

Further details of the present invention will become apparent from the following description of the embodiments and the appended drawings which illustrate the examples of the invention.

The drawings illustrate:

FIG. 1: a representation of a perspective visualized three dimensional object with an automatically appended description derived from morphological attributes.

Figure 2:
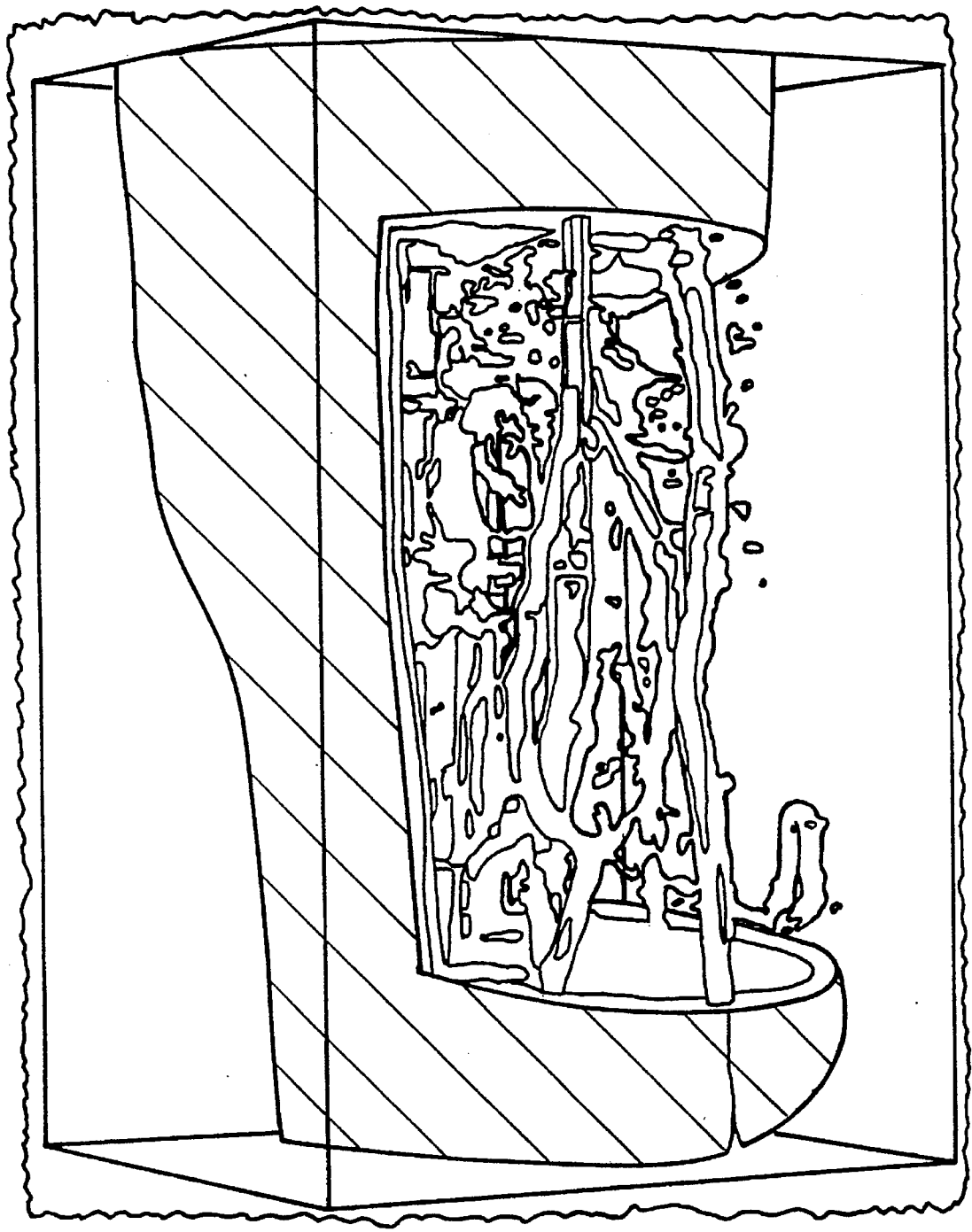

FIG. 2: a perspective representation of a body part, where relative to given sectional cuts of a blood vessel system is represented without surrounding tissue.

Figure 3:
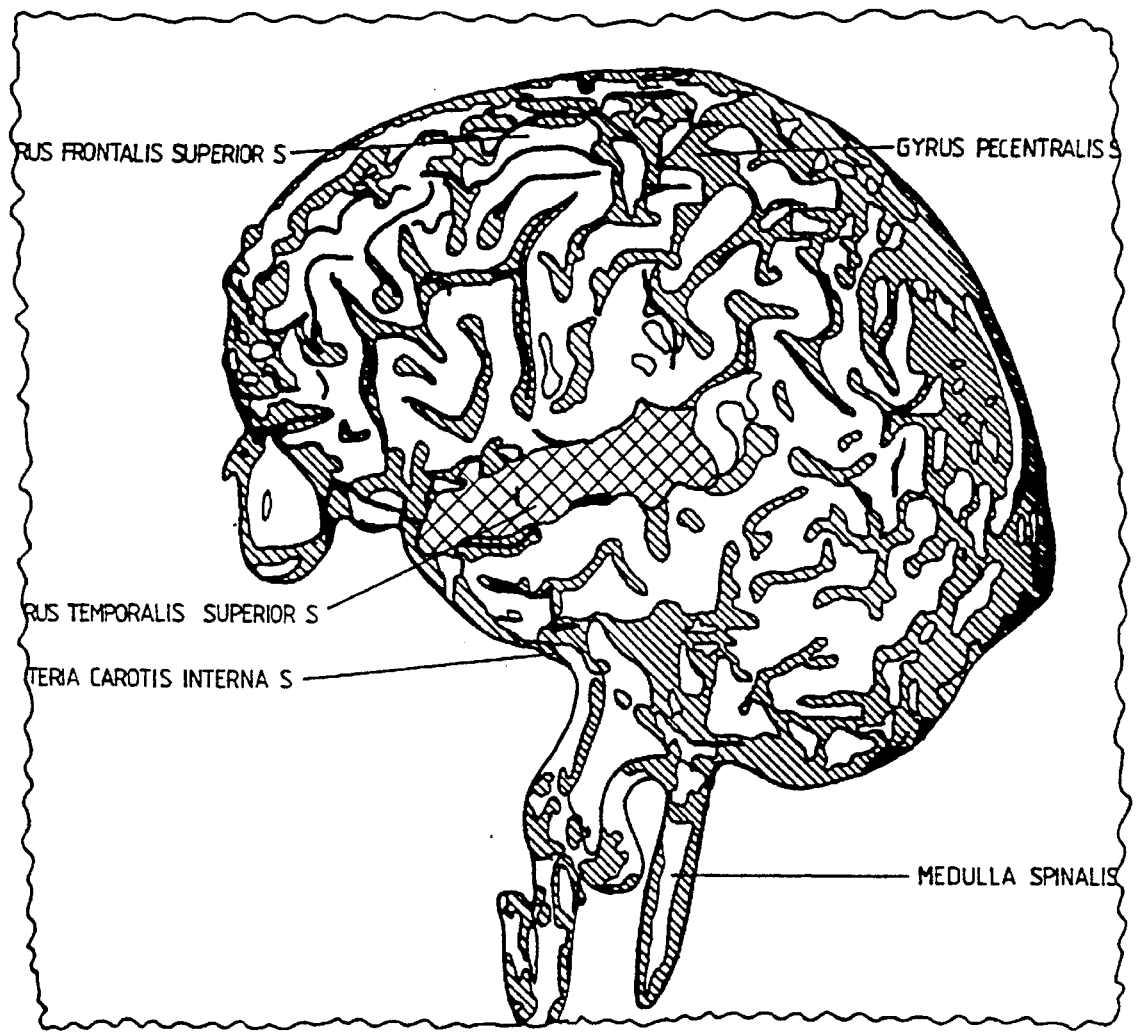

FIG. 3: a side view of a visualized brain with a marked area where sub-objects were automatically combined with textual information when they are pointed at by the user.

Figure 4:
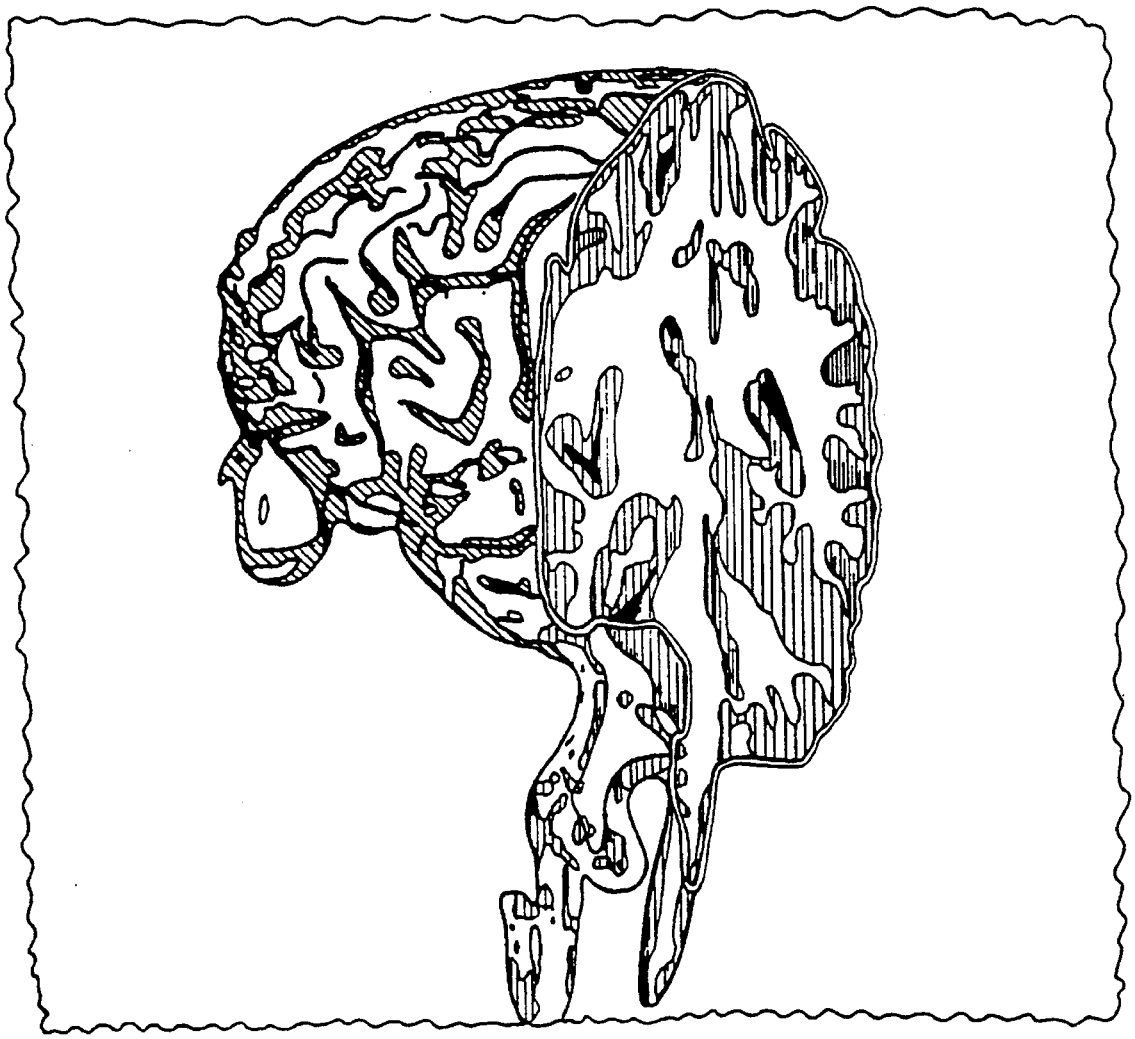

FIG. 4: a section through the object according to FIG. 3.

Figure 5:
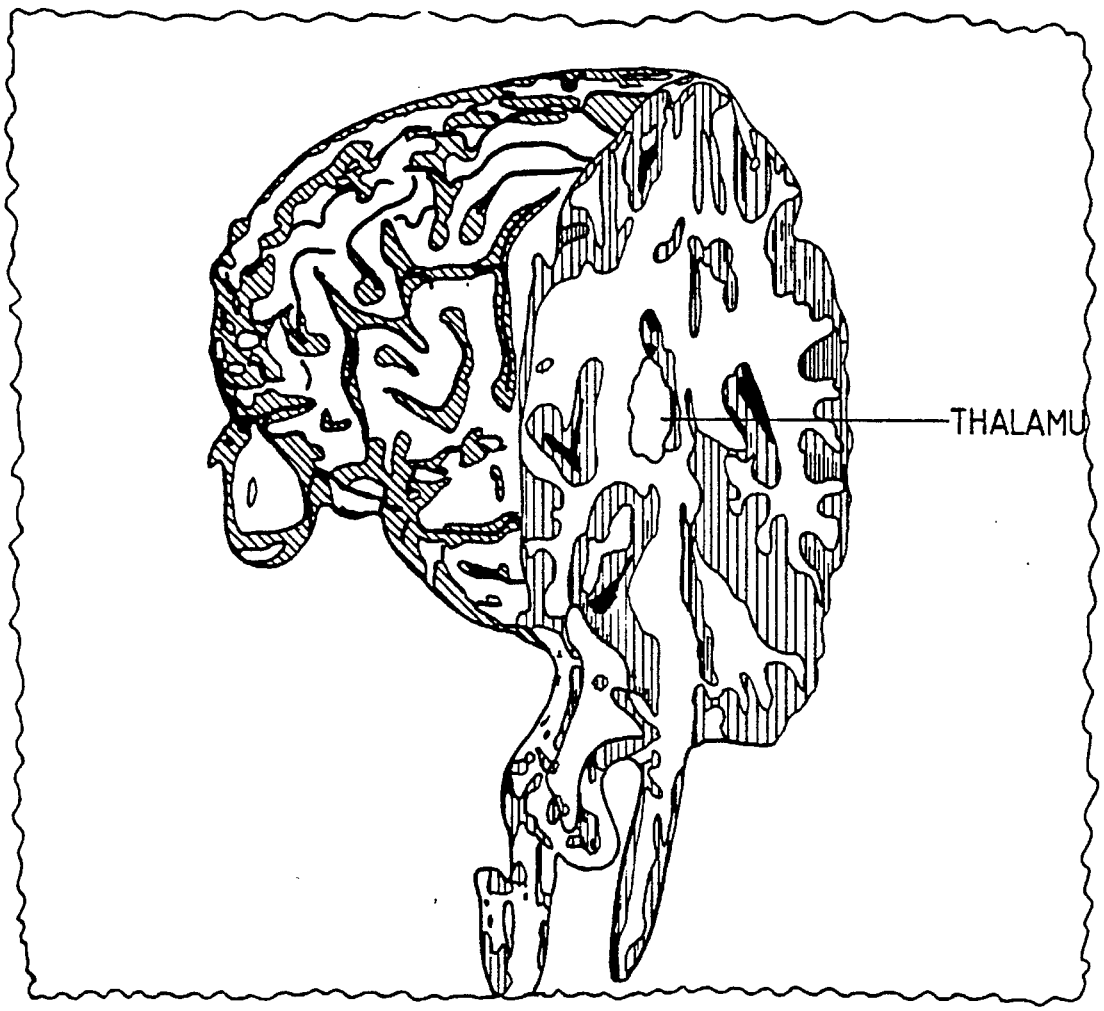

FIG. 5: a section through the object according to FIG. 3, provided with textual information and an arrow oriented to the object.

Figure 6:
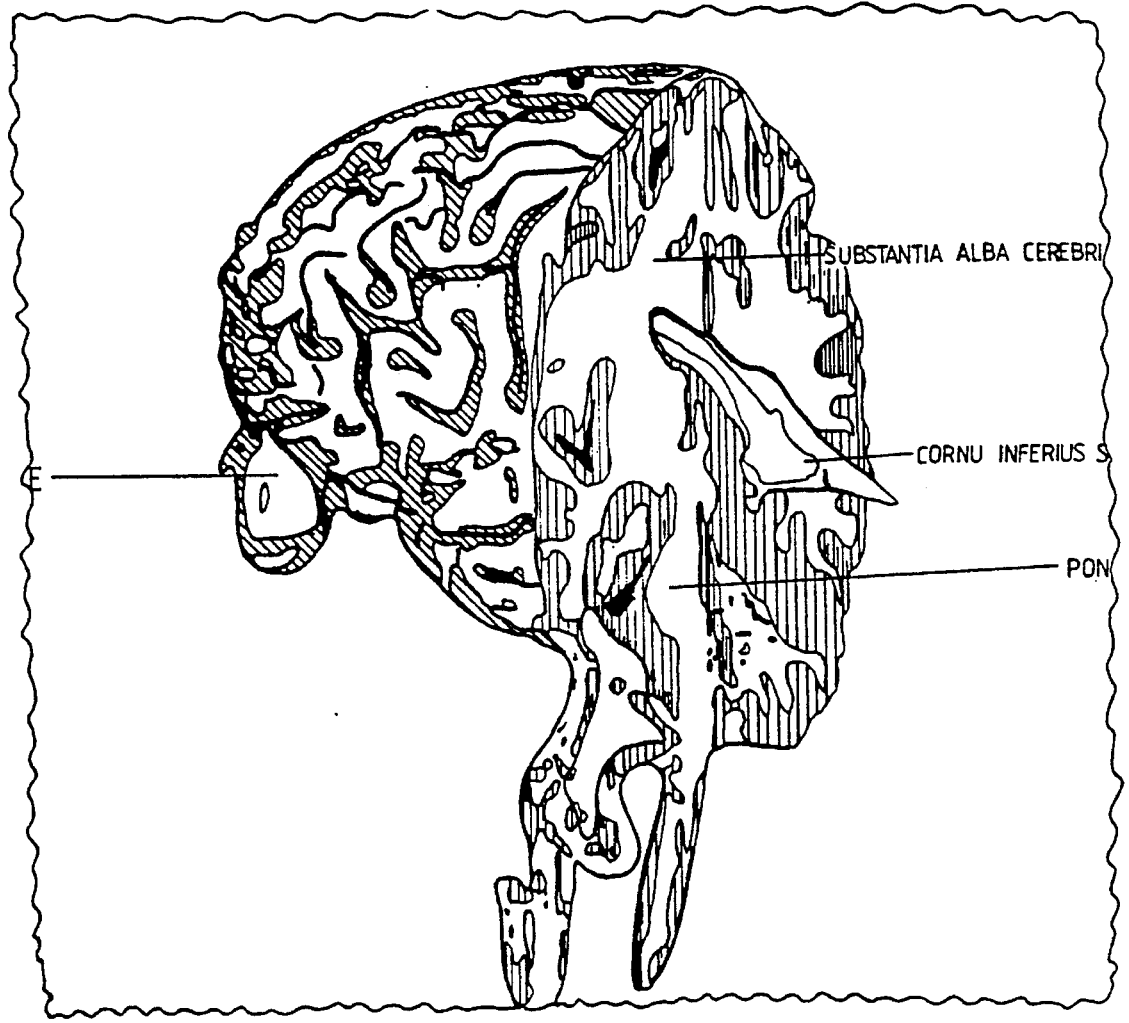

FIG. 6: a section through the object according to FIG. 3 wherein, based on the volume element information, a surface area projects out of the sectional surface represented.

Figure 7:
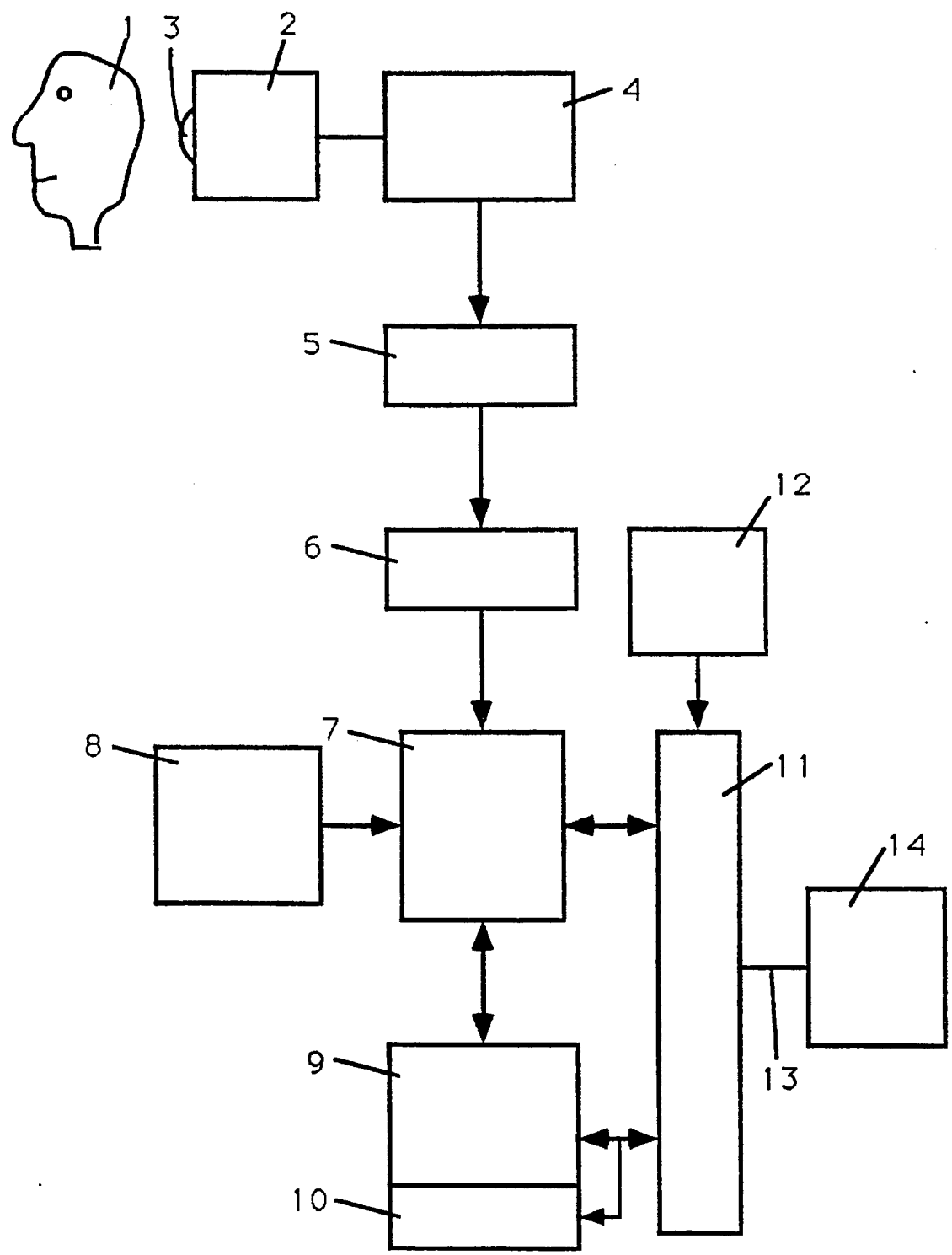

FIG. 7: a block diagram of a device for representation of a three dimensional object.

Figure 8:
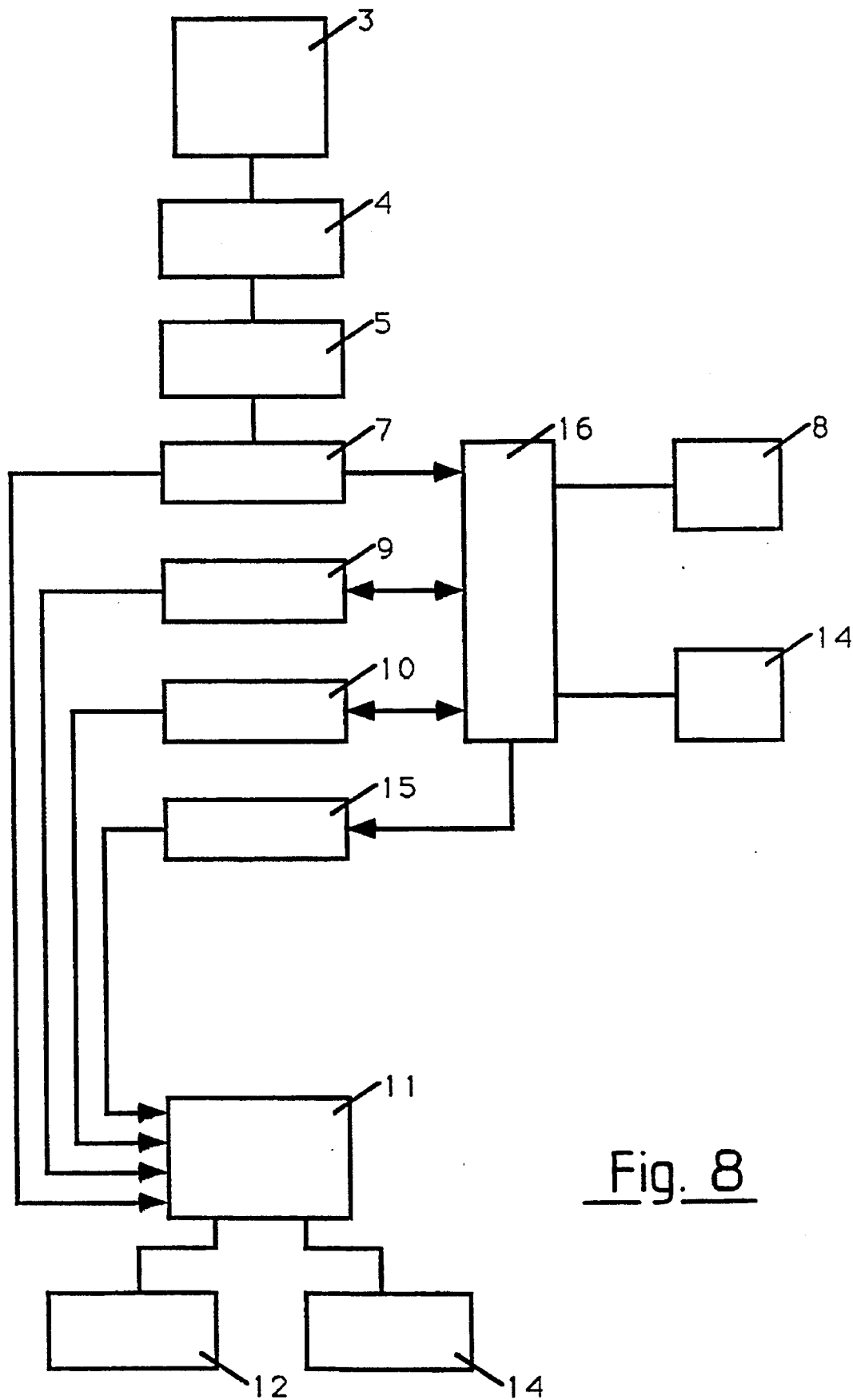

FIG. 8: a block diagram of another device for representation of three dimensional objects.

Figure 9:
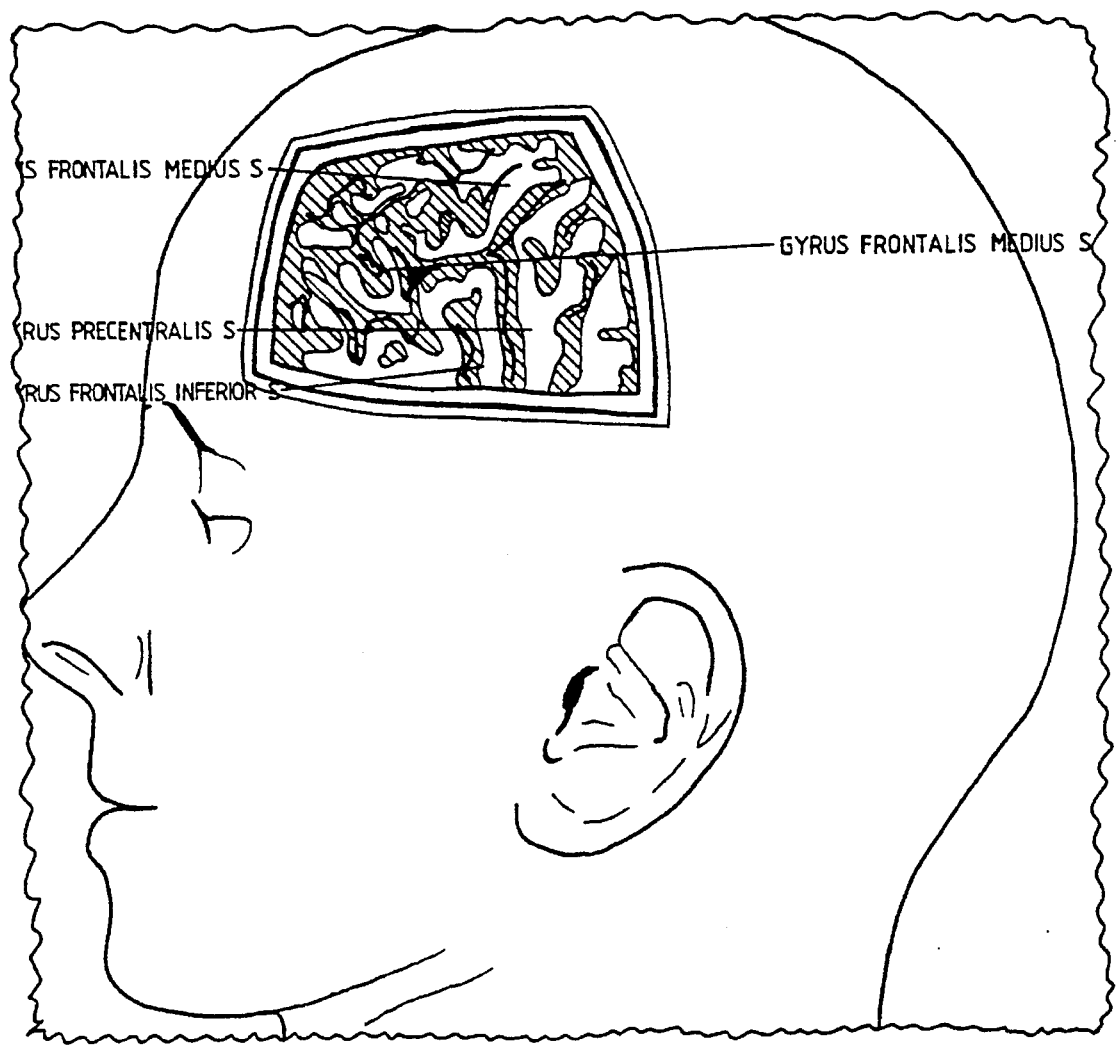
Figure 10:
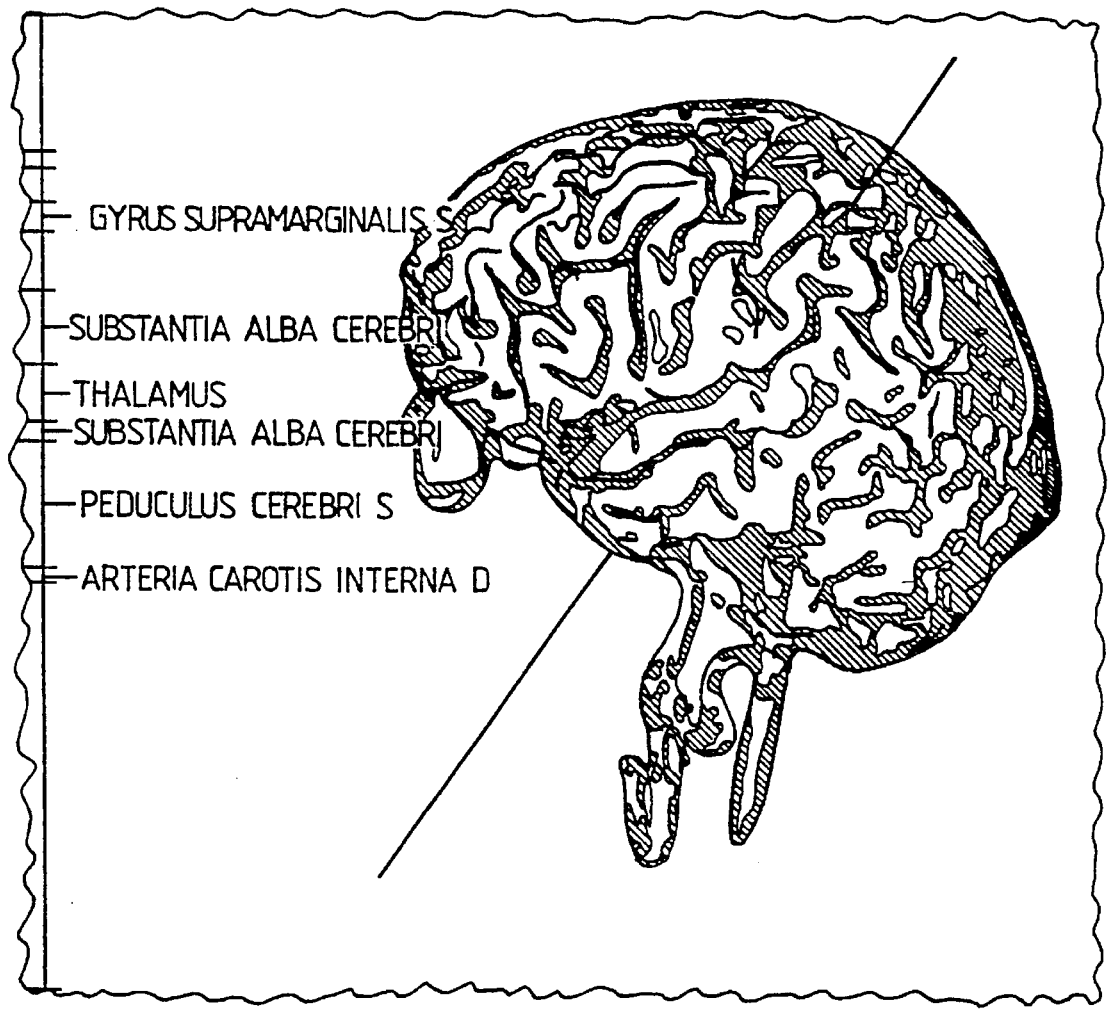

FIG. 9: a representation of a visualized object as can be used for practice of neurosurgical operations and FIG. 10: a view of another object whereby volume element information (morphological attributes) is separately represented along a projected path in order to find the optimum entrance access for a stereotactic operation.

A device for the representation of a three dimensional object (1) includes, according to the representation in FIG. 7, an acquisition unit (2), which with help of at least one detector (3) captures spatial measured value of three dimensional objects (1). For example the sectional picture sequences determined therefrom are led to a storage device (4). With help of an interpolator (5) the intermediate areas of the respective sectional pictures which were not recorded are reconstructed and subjected to a subdivision of volume elements by a separator (6). It is especially intended to generate volume elements of identical spatial elongation, e.g. cubes. This has the advantage that the respective coordinates relating to the volume elements can be stored at comparatively small expense. However, it is possible in principle to provide volume elements of varying elongations for various resolution areas.

Instead of generating sectional pictures, it is also possible to undertake a grid-type acquisition of the object (1) and to gain measured value information depending on a selectable grid system. The respective grid points could be arranged by subdividing an object (1) into cube shaped volume elements, for example, on the corners of the respective cubes. However, it is also possible, independently of an intended form for the volume elements, to take other grids at the acquisition of the measured value information and, for example, providing a spiral shaped acquisition path along which information will be established at a constant or variable distance.

The coordinates assigned to the volume elements as well as, if necessary, incorporated geometric parameters e.g. gray value, are recorded in a measured value volume storage device. The measured value volume storage device (7) links with an input device (8), which enables the respective volume elements to be assigned to attributes, which are stored in the attribute storage device (9). It is especially possible to embody the respective attributes corresponding assignment of meaning as textual information in the equivalence bank (10).

The measured value volume bank (7) and the attribute bank (9) are linked to a control unit (11) which, in dependence of requests, given with help of an operating device (12), determines a combination of volume elements and attributes. Depending on the volume elements to be represented as well as the respectively assigned attributes, the resulting picture information is conveyed over a transference span (13) to a representation device (14). It is especially advantageous to combine the operating device (12) and the input device (8) as an integrated instrument.

The representation equipment (14) can, for example, be adapted as a display screen. It is, however, also especially possible to adapt the representation equipment (14) as a print carrier which records pictures as well as descriptive elements for the realization of medical atlases in book form.

According to the embodiment of FIG. 8, a separate assignment control unit (16) is provided to enable input applications which is connected with the input device (8) as well as with the representation equipment (14). The assignment control unit (16) is connected through a linking storage device (15) to the control unit (11). In the linking bank (15) higher level information may be stored which, in the visualization of a brain, for example, links the substructures taking part in the path of auditive stimuli. With help of operating equipment (12) it is possible to provide operator input for visualization and e.g., according to a graphic selection of a particular portion of an object, determine a textual fade in of a description of the object portion with help of the equivalence bank (10). It is however also possible, in reverse sequence, to choose at least one of these descriptions from a projected index of descriptions and to automatically mark the respective object portion.

In a representation according to FIG. 1 the three dimensional object (1) is depicted as a human head, through which an essentially horizontal section is shown. Due to the attributes respectively assigned to the volume elements, it is possible to generate a surface development projecting from the sectional plane. To facilitate understanding of the represented picture elements, text is generated which is assigned to respectively chosen attributes.

From the representation in FIG. 2 it can be seen that an arbitrarily selected sectional development is realized and, in dependence of respectively chosen attributes, a three dimensional representation of the chosen body elements can be generated.

The FIGS. 3 through 6 illustrate how various picture information can be arranged due to the structuring in volume elements and the respective attribute assignment.

Assignment of the attribute is appropriately executed by an expert conversant in the matter or automatically with aid of a picture analysis unit, which provides at least first estimates of the attribute. The expert can so proceed that, first of all, in a side view of the object according to FIG. 3, a particular area is characterized with the corresponding attribute. The regions assigned in the respective areas of the sectional pictures can be further marked by a subsequent analysis of the respective sectional picture and thereby facilitate orientation for the expert. Thus, the information density can be sequentially increased and within using the system in later applications the expert is allowed to make a combination of picture segments, which he has not yet encountered in this form in practice and so an operation situation can be prepared.

With use of the device in an educational field it is possible to try out all essential preparation techniques and to practice what may come about when working with actual objects. In contrast to working on an actual object, certain work steps which otherwise would not be satisfactorily carried out, however arbitrarily often repeated, equalize existing deficits of knowledge. It is possible to place exclusive pictorial information at the disposal of a student and according to a partial or complete execution of the provided capabilities through arranging a blend of textual information or certain color deposits to arrange information about which body elements he has actually treated. With a diagram of the proposed course of work it is possible to assess the appropriateness of a chosen work sequence.

Aside from using an individual series of sectional pictures, it is also possible to use a plurality of sectional picture series as a basis of the stored picture information. Hereby it is possible to combine various examination methods with various established picture contents and to increase the information content. Due to the assigned volume element information, pictures of a particular technique which are established with help of another technique can also be derived from picture information. For example, it is possible, based on volume elements and coordinated attributes, which are generated as a result of computer tomographic pictures, to establish picture processes which correspond to an x-ray picture. Due to the attributes of the respective volume elements, it can be determined if the corresponding volume element demonstrates a shadow in an x-ray photograph and what intensity the shadow has.

Aside from assigning attributes corresponding to the qualities discussed in single individual cases, e.g. the relationship to a particular organ, it is also possible to provide attributes with coloring by anatomical sectional elements or an intensity value of element derived from magnetic resonance tomography, it is also possible to provide attributes which correspond to a statistical probability of the appearance of the object variations. With such an assignment, for example, in the area of arbitrarily selected sectional pictures a probability distribution for the occurrence of certain tumors can be generated. Such a probability representation enables a doctor in the training phase to raise his sensitiveness regarding certain structural variations. With an interpretation of concrete picture information which is related to a particular patient, it is possible to carry out an automatic preliminary examination with a comparison to the standard picture information and with this preliminary examination to determine deviations from a structure interpreted as "normal" and an actual structure. Thus, the doctor's attention can be turned to deviations from the normal tissue distribution and tissue structures, thereby achieving a higher certainty relative to a complete incorporation of pathological variations.

Various devices can be used as incorporation devices (2). Aside from devices for acquisition of microscopic or macroscopic sectional sequences it is especially advantageous to use computer tomography or magnetic resonance tomography. It is also possible to use devices for execution of a positron emission tomography or single photon tomography. Further possibilities exist in the use of ultrasound devices, devices for execution of a magneto-encephalography or devices for execution of a multiplanar x-ray angiography. In addition or alternately to a spatial picture sequence, it is also possible to use temporal picture sequences by using the dynamics of the sequence, for example demonstrating the course of a beating heart. The spatially or temporally established picture sequences could also be supplemented with the aforementioned manual structural input. It is also possible to include volume elements from a draftsman through an input device.

Aside from assignment to the aforementioned intensity values and characterizing anatomical regions, the attributes could be used to characterize functional regions, e.g. the speech center in the brain or to characterize help regions, e.g. a target volume in radiation therapy planning. Boundaries of the respective regions can be gained through various intensities of the sectional picture sequences or by complex judgment criteria determined by an expert versed in the subject matter. Independent of the actual spatial form, the above mentioned probability for the appearance of tissue variations and an intensity profile for a therapy that may need to be executed. In a radiation therapy further regions can be characterized by the attributes and also represent, for example, a ray dose as well as ray direction and intensity.

In addition or alternately to the morphological links which can be achieved with help of attributes, it is also possible to undertake functional combinations and to illustrate for example a stimulation process via a suitable attribute assignment.

I claim:

1. A method for the representation of a three dimensional object especially for use in the field of medical technology utilizing a computer based system with a screen and at least one input device, said computer based system having an interactive system implemented thereon, wherein the complete volume of the three dimensional object is acquired spatially relative to a geometric parameter, a sequence of picture units are generated as well as a spatial coordination of the parameter and are stored in a storage device and fed to a representation device for visualization, said interactive system enabling the selection of at least one part of a displayed picture unit and said system being able to display said selected part of said picture without displaying other parts of said picture in the same way as said selected part, said method of representation comprising after acquisition, subdividing the complete volume assigned to an object into volume elements, assigning at least one attribute defining each of said volume elements thereto, said attribute corresponding to one biological characteristic of said volume elements, all volume elements of the selected part of said displayed picture unit having at least one identical attribute, each of said volume elements being filled and the complete content of each volume element having the same attribute and the coordinates of each of the volume elements and storing said attribute characterizing each of the volume elements and subsequently carrying out an assignment of the volume elements to recombine selected volume elements to create spatial substructures of the object as well as for visualization of a selectable coordination of the volume elements realized dependent on at least one selected attribute, said recombination of said volume elements being a function of selecting at least one free selectable attribute, said at least one free selectable attribute being selected by an analysis of readable text selected by the user, said selected readable text defining the meaning of said attributes, combining all volume elements defined by said selected attribute for said recombination within the complete content of the object, assigning and storing meanings of each of said attributes, displaying said meanings of said attributes as readable text after selection of one portion of the object, whereby the recombination of said selected volume elements creates a visualization of a selected portion of a real biological object, said interactive system also being able to automatically combine said selected part of said picture with said meanings of said attributes as readable text on said screen.

2. A method according to claim 1 characterized in that the visualization is carried out dependent on the attributes and under consideration of an optical combination of the attributes with the spatial portional structure for realization of a given view.

3. A method according to claim 2 characterized in that said visualization comprises producing a digital picture.

4. A method according to claim 3 characterized in that visualization is carried out in a display device (14) which creates an image on a screen.

5. A method according to claim 3 characterized in that visualization is carried out in a display device (14) which creates an image on a print carrier.

6. A method according to claim 2 characterized in that by a measured technical acquisition of the object (1), a sequence of essentially two dimensional pictures is generated.

7. A method according to claim 6 characterized in that said measured technical acquisition comprises creating a spatial picture sequence.

8. A method according to claims 2 characterized in that at least portions of the object (1) are linked logically with different attributes in an attribute combination.

9. A method according to claim 1 characterized in that at visualization, at least one portion of the volume elements assigned to be recombined is compared with at least a portion of volume elements which are assigned to an object to be analyzed.

10. A method for the representation of a three dimensional object especially for use in the field of medical technology, wherein the complete volume of the three dimensional object is acquired spatially relative to a geometric parameter, a sequence of essentially two dimensional picture units are generated by a measured technical acquisition as well as spatial coordination of the parameter and are stored in a storage device and fed to a representation device for visualization, said method of representation comprising after acquisition, subdividing the complete volume assigned to an object into volume elements, assigning at least one attribute defining each of said volume elements thereto, said attribute corresponding to one biological characteristic of said volume elements, each of said volume elements being filled and the complete content of each volume element having the same attribute and the coordinates of each of the volume elements and storing said attribute characterizing each of the volume elements and subsequently carrying out an assignment of the volume elements to recombine selected volume elements to create spatial substructures of the object as well as for visualization of a selectable coordination of the volume elements realized dependent on at least one selected attribute, said recombination of said volume elements being a function of selecting at least one free selectable attribute, said at least one free selectable attribute being selected by an analysis of readable text selected by the user, said selected readable text defining the meaning of said attributes, combining all volume elements defined by said selected attribute for said recombination within the complete content of the object, assigning and storing meanings of each of said attributes, displaying said meanings of said attributes as readable text after selection of one portion of the object, whereby the recombination of said selected volume elements creates a visualization of a selected portion of a real biological object, said visualization is carried out dependent on the attributes and under consideration of an optical combination of the attributes with the spatial portional structure for realization of a given view, said measured technical acquisition comprises creating a temporal picture sequence.

11. A method for the representation of a three dimensional object especially for use in the field of medical technology, wherein the complete volume of the three dimensional object is acquired spatially relative to a geometric parameter, a sequence of picture units are generated as well as a spatial coordination of the parameter and are stored in a storage device and fed to a representation device for visualization, said method of representation comprising after acquisition, subdividing the complete volume assigned to an object into volume elements, assigning at least one attribute defining each of said volume elements thereto, said attribute corresponding to one biological characteristic of said volume elements, each of said volume elements being filled and the complete content of each volume element having the same attribute and the coordinates of each of the volume elements and storing said attribute characterizing each of the volume elements and subsequently carrying out an assignment of the volume elements to recombine selected volume elements to create spatial substructures of the object as well as for visualization of a selectable coordination of the volume elements realized dependent on at least one selected attribute, said recombination of said volume elements being a function of selecting at least one free selectable attribute, said at least one free selectable attribute being selected by an analysis of readable text selected by the user, said selected readable text defining the meaning of said attributes, combining all volume elements defined by said selected attribute for said recombination within the complete content of the object, assigning and storing meanings of each of said attributes, displaying said meanings of said attributes as readable text after selection of one portion of the object, whereby the recombination of said selected volume elements creates a visualization of a selected portion of a real biological object, at least one of the coordinates of each of the volume elements is assigned to a structured attribute combination.

12. A method for the representation of a three dimensional object especially for use in the field of medical technology, wherein the complete volume of the three dimensional object is acquired spatially relative to a geometric parameter, a sequence of picture units are generated as well as a spatial coordination of the parameter and are stored in a storage device and fed to a representation device for visualization, said method of representation comprising after acquisition, subdividing the complete volume assigned to an object into volume elements, assigning at least one attribute defining each of said volume elements thereto, said attribute corresponding to one biological characteristic of said volume elements, each of said volume elements being filled and the complete content of each volume element having the same attribute and the coordinates of each of the volume elements and storing said attribute characterizing each of the volume elements and subsequently carrying out an assignment of the volume elements to recombine selected volume elements to create spatial substructures of the object as well as for visualization of a selectable coordination of the volume elements realized dependent on at least one selected attribute, an attribute for characterizing the probability of an appearance of structure variations is assigned to at least one of the volume elements, said recombination of said volume elements being a function of selecting at least one free selectable attribute, said at least one free selectable attribute being selected by an analysis of readable text selected by the user, said selected readable text defining the meaning of said attributes, combining all volume elements defined by said selected attribute for said recombination within the complete content of the object, assigning and storing meanings of each of said attributes, displaying said meanings of said attributes as readable text after selection of one portion of the object, whereby the recombination of said selected volume elements creates a visualization of a selected portion of a real biological object.

13. A method according to claim 12 characterized in that at least to some of the volume elements attributes concerning functional associations are assigned.

14. A method according to claim 13 characterized in that at least one of the attributes is associated with text.

15. A method according to claim 13 characterized in that at least one portion of the object (1) is recorded by measurement with help of computer tomography.

16. A method according to claim 13 characterized in that at least one portion of the object (1) is recorded by measurement with help of magnetic resonance tomography.

17. A method according to claim 13 characterized in that at least one portion of the object (1) is recorded by measurement with help of an x-ray examination.

18. A method according to claim 13 characterized in that at least one portion of the object (1) is recorded by measurement with help of an ultrasound examination.

19. A method according to claim 13 characterized in that at least one portion of the object (1) is recorded by measurement with help of a sequence of anatomical cross sectional cuts.

20. A method according to claim 13 characterized in that at least one portion of the object (1) is recorded by measurement with help of magneto encephalograph.

21. A method according to claim 13 characterized in that at least one portion of the object (1) is recorded by measurement with help of positron-emission-tomography.

22. A method according to claim 13 characterized in that at least one portion of the object (1) is recorded by measurement with help of single-photon emissions tomography.

23. A method according to claim 13 characterized in that the object (1) is completely subdivided into volume elements.

24. A method according to claim 23 characterized in that volume elements are combined according to a preselected criteria to characterize functional regions of said object.

* * * * *